United States Patent [19]

Yamamoto et al.

[11] Patent Number: 4,891,431
[45] Date of Patent: Jan. 2, 1990

[54] PROCESS FOR PREPARING 2-UNSUBSTITUTED IMIDAZOLES

[75] Inventors: Sanehiro Yamamoto, Iwakuni; Mitsuki Yasuhara, Ichihara; Fujihisa Matsunaga, Ichihara; Masato Okano, Ichihara; Mitsunori Nakamura, Ichihara, all of Japan

[73] Assignee: Mitsui Petrochemical Industries, Ltd., Tokyo, Japan

[21] Appl. No.: 107,799
[22] PCT Filed: Jan. 28, 1987
[86] PCT No.: PCT/JP87/00057
§ 371 Date: Sep. 25, 1987
§ 102(e) Date: Sep. 25, 1987
[87] PCT Pub. No.: WO87/04431
PCT Pub. Date: Jul. 30, 1987

[30] Foreign Application Priority Data

Jan. 28, 1986 [JP] Japan .................................. 61-16617
Mar. 31, 1986 [JP] Japan .................................. 61-73397
Dec. 18, 1986 [JP] Japan ................................. 61-302633

[51] Int. Cl.$^4$ ............................................ C07D 233/58
[52] U.S. Cl. ...................................... 548/335; 548/346
[58] Field of Search ............................ 548/335, 346

[56] References Cited

PUBLICATIONS

Bredereck et al., *Chem. Ber.*, vol. 86, p. 88, 1953.

*Primary Examiner*—Mary C. Lee
*Assistant Examiner*—Zinna Northington-Davis
*Attorney, Agent, or Firm*—Sherman and Shalloway

[57] ABSTRACT

A process for preparing 2-unsubstituted imidazoles which comprises reacting an α-hydroxycarbonyl compound with a formamide in such amounts as to make the molar ratio of said formamide to said hydroxycarbonyl compound not more than 2 at a reaction temperature of 100°–170° C. in an atmosphere of ammonia gas. According to this process, 2-unsubstituted imidazoles may be obtained in very high yields. In addition, because no great excess of formamide is used in carrying out the reaction, an effect of not requiring the recovery operation incident to decomposition of formamide is obtained as well. And by removing formic acid formed as a by-product by the reaction, a reactor and separation equipment such as a distillation column are not corroded, and imidazoles of a high purity can be obtained.

14 Claims, 2 Drawing Sheets

FA / HC MOLAR RATIO

PROCESS FOR PREPARING 2-UNSUBSTITUTED IMIDAZOLES

TECHNICAL FIELD

The present invention relates to a process for preparing imidazoles. More particularly, the present invention relates to a process for preparing 2-unsubstituted imidazoles in high yields by reacting α-hydroxycarbonyl compounds with formamide under specified conditions.

BACKGROUND TECHNOLOGY

Imidazoles are very useful compounds not only as starting materials for producing medicines and agricultural chemicals, but also as curing agents or curing accelerators for epoxy resins, industrial sterilizers, rust inhibitors and antistatic agents. Especially, 2unsubstituted imidazoles are useful compounds for producing antitumor agents for the digestive organs or curing agents for epoxy resins.

Such 2-unsubstituted imidazoles have heretofore been prepared by, for example, reacting a 1,2-dicarbonyl compound with an aldehyde and ammonia. However, this process has the disadvantage in that the material 1,2-dicarbonyl compound cannot be produced on a mass production scale. A process for preparing 2-unsubstituted imidazoles by reacting an α-hydroxyketone with ammoniacal cupric acetate in the presence of an aldehyde has also been known. However, this process has had a problem in that the yield of the obtained imidazoles is low, the steps are complicated and a large amount of expensive cupric acetate is consumed. Further, it has been known that when an imidazoline obtained by reacting a 1,2-diamine with a cyanogen compound is dehydrogenated in the presence of a nickel formate catalyst, an imidazole is obtained. However, this process also has a problem in that it cannot give 2-unsubstituted compounds.

In order to solve these problems, a process for preparing imidazoles by mixing an α-hydrpxycarbonyl compound (hereinafter may be referred to as HC) and a formaldehyde amide (hereinafter may be referred to as FA) at an FA/HC molar ratio of 10-20 and reacting them at a temperature of 180° C.-200° C. was proposed (see Chem. Ber., 86, page 88, 1953).

According to this process, when the FA/HC molar ratio is made 10-20, imidazoles are obtained in a yield of 50-90%, but when the FA/HC molar ratio is made 2 which is the stoichiometric ratio, the yield of imidazoles decreases to as low as 10-20%. Because of this, the reaction has to be carried out at an FA/HC molar ratio of 10-20. As a result, after completion of the reaction, a large amount of unreacted FA must be recovered by distillation. Because FA is unstable and tends to be decomposed, as much as 30-40% of FA is lost during distillation. Because of this, in order to bring the FA/HC molar ratio close to 2 which is the stoichiometric ratio, a method in which HC is gradually added to FA while keeping the pH of the reaction liquid at 4-10 was also proposed (see Japanese Laid-Open Patent Publication No. 30574/1986 laid open on Feb. 12, 1986).

However, there is still a problem in that when the FA/HC molar ratio is made 2 or less, the yield of imidazoles became about 40%, and the imidazoles cannot be obtained in high yields.

The present inventors conducted strenuous studies with a view to obtaining 2-unsubstituted imidazoles in high yields from FA and HC, and as a result found that when the reaction is carried out under specified conditions, even if the FA/HC molar ratio is not more than 2, it is possible to obtain 2-unsubstituted imidazoles in high yields. This finding has led to completion of the present invention.

An object of the present invention is to solve such problems of the prior art as mentioned above and provide a process capable of preparing 2-unsubstituted imidazoles in high yields from FA and HC even if the FA/HC molar ratio is not more than 2.

Another object of the present invention is to provide a method of removing by-product formic acid in the preparation of imidazoles from an α-hydroxycarbonyl compound and formamide, in which the corrosion of a separating device such as a distillation column is inhibited by efectively removing the by-product formic acid from the reaction mixture.

Further objects and advantages of the present invention will become apparent from the following description.

According to the present invention, such objects and advantages of the present invention are achieved by a process for preparing 2-unsubstituted imidazoles represented by the general formula (II)

wherein $R^1$ and $R^2$ may be the same or different, and each represents a hydrogen atom, an alkyl group, a cycloalkyl group, an aryl group or an arylalkyl group, which comprises reacting an α-hydroxycarbonyl compound represented by the general formula (I)

wherein $R^1$ and $R^2$ are the same as defined above, with a formamide in such amounts as to make the molar ratio of said formamides to said hydroxycarbonyl compound not more than 2 at a reaction temperature of 100°-170° C. in an atmosphere of ammonia gas.

The reaction of the present invention may be expressed by the following reaction formula (A).

The reaction formula shows a case wherein as the formamide, formamide ($HCONH_2$) is used.

The α-hydroxycarbonyl compound (HC) used in the present invention is represented by the general formula (I) wherein $R^1$ and $R^2$ may be the same or different and each represents a hydrogen atom, an alkyl group, a cycloalkyl group, an aryl group or an arylalkyl group.

The alkyl group may be a straight chain or branched chain alkyl group, preferably having 1-14 carbon atoms. As such alkyl group, there may be illustrated, for example, methyl, ethyl, n-propyl, iso-propyl, n-butyl, iso-butyl, sec-butyl, t-butyl, n-pentyl, n-hexyl, n-heptyl and n-octyl.

The cycloalkyl group preferably has a carbon ring member of 4-8 carbon atoms. The cycloalkyl group may be substituted by an alkyl group having 1-10 carbon atoms, more preferably 1-3 carbon atoms. As such cycloalkyl group, there may be illustrated, for example, cyclopentyl, cyclohexyl and p-methyl cyclohexyl.

The aryl group is, for example, a phenyl, naphthyl or anthranyl group, and these groups may be substituted by an alkyl or alkoxy group having, for example, 1-10 carbon atoms, more preferably 1-4 carbon atoms.

The arylalkyl group consists of an aryl moiety of, for example, a phenyl, naphthyl or anthranyl group and an alkyl moiety of a straight chain or branched chain alkyl group having, for example, 1-14 carbon atoms, more preferably 1-10 carbon atoms. The aryl moiety may be substituted by an alkyl or alkoxy group having, for example, 1-10 carbon atoms, more preferably 1-4 carbon atoms.

As the HC represented by general formula (I), for example, the following compounds may be illustrated.

Aliphatic carbonyl compounds wherein $R^1$ is a hydrogen atom or an alkyl group:

Hydroxyacetone (acetol), acetoin, iso-butyroyliso-propylcarbinol, tert-valeroyl-tert-butylcarbinol, n-butyroyl-n-propylcarbinol, n-propionylethylcarbinol, hexanoylpentylcarbinols, acetylethylcarbinol, acetylphenylcarbinol, formyl-p-tolylcarbinol, etc.

Alicyclic carbonyl compounds wherein $R^1$ is a cycloalkyl group:

(Cyclohexylacetyl)-methylcarbinol, (p-cyclohexylformyl)-ethylcarbinol, (cyclohexanoyl)-cyclohexylcarbinol, etc.

Aromatic carbonyl compounds wherein $R^1$ is an aryl group:

Benzoin, p-toluyl-p-tolylcarbinol, benzoylmethylcarbinol, m-toluyl-tert-butylcarbinol, α-naphthoylmethylcarbinol, p-anthranoyl-ethylcarbinol, etc.

Arylalkylcarbonyl compounds wherein $R^1$ is an arylalkyl group:

(Phenylacetyl)-benzylcarbinol, (p-anisyl-n-propionyl)-methylcarbinol, etc.

The formamide (FA) used in the present invention is meant to include formamide, its oligomer or polymer or an adduct or a complex of formamide with another compound.

As the formamide adduct of formamide and another compound, for example, a sodium hydrogensulfite adduct and a hydrogen cyanide adduct may be cited.

Usually, formamide is preferably used as the formamide.

In the present invention, HC and FA are reacted under specified reaction conditions. These reaction conditions will be explained hereinbelow.

The amounts of HC and FA are so selected as to provide a final FA/HC molar ratio of not more than 2, preferably 1-2. This ratio is a molar ratio between FA and HC which are used until the reaction is completed. Accordingly, this ratio is not necessarily in accord with the FA/HC molar ratio in the reaction system during the progress of the reaction after adding HC to FA.

It is preferable to carry out the reaction of HC with FA while adding gradually HC little by little to FA. The hourly rate of adding HC to FA is preferably 0.01-1, more preferably 0.02-0.2 mol, per mol of FA.

In the present invention, the reaction of HC with FA is advanced in an atmosphere of ammonia gas. In order to advance the reaction in an atmosphere of ammonia gas, ammonia gas is introduced into the reaction system.

It is desirable that the amount of ammonia gas supplied to the reaction system before the initiation of the reaction and throughout the reaction is such that the $NH_3/FA$ (molar ratio) is preferably 0.1-10, more preferably 1-5. According to the present invention, the yield of the product 2-unsubstituted imidazoles is increased by carrying out the reaction in an atmosphere of ammonia gas.

The reaction of HC with FA is carried out normally at 100°-170° C., preferably at 130°-140° C. When the reaction temperature exceeds 170° C., the yield of the obtained 2-unsubstituted imidazoles undesirably decreases. On the other hand, reaction temperatures of less than 100° C. are undesirable because the rate of reaction between HC and FA becomes too slow.

The reaction of HC with FA is carried out normally under the pressure of 0-50 $Kgf/cm^2G$, preferably 5-15 $Kgf/cm^2G$.

The reaction according to the present invention is normally carried out using a vessel-type reactor, but it can also be carried out using other types of reactor.

The reaction of HC with FA in an atmosphere of ammonia gas according to the present invention is, as mentioned above, preferably carried out by adding gradually HC little by little to FA, but specifically, it may be carried out as follows.

(a) A reactor is charged with FA, to which HC and ammonia gas are separately supplied gradually little by little.

(b) A reactor is charged with FA, to which a mixture of HC and ammonia gas is supplied gradually little by little.

(c) A reactor is charged with FA and ammonia gas, to which HC is supplied gradually little by little.

(d) A reactor is charged with FA and ammonia gas, to which HC and ammonia gas are separately supplied gradually little by little.

(e) A reactor is charged with FA and ammonia gas, to which a mixture of HC and ammonia gas is supplied gradually little by little.

In each of the aforesaid cases, the reaction of HC with FA may be carried out in a completely closed system, or in a flow system in which a gas or vapor in the gaseous phase is withdrawn little by little to the outside of the system while controlling the pressure.

Again, in each of the aforesaid cases, HC and ammonia gas may be supplied to either one of the gaseous phase or the liquid phase inside the reactor.

Thus, according to the process of the present invention, with the intended product of imidazoles, a large amount of formic acid is produced as a by-product. Formic acid is produced, as mentioned above, as a by-product according to the reaction formula (A). It is also formed by the hydrolysis of the starting formamide as shown by the following reaction formula (B):

Formic acid formed is present in an amount as much as 10–50% by weight in the reaction liquid which is a reaction mixture after completion of the reaction.

At a time of completion of the reaction referred to in the present invention should be understood as at a time when preferably at least 80%, more preferably at least 90%, especially at least 95% of HC added to the reaction system has been consumed.

When the reaction liquid as obtained is directly distilled for the purpose of obtaining the desired imidazole from the reaction liquid containing such a large amount of formic acid, the distillation column undergoes marked corrosion even if it is made of high grade stainless steel having the highest possible corrosion resistance. For solving such a problem, the present inventors attempted (a) a method of neutralizing formic acid by adding an aqueous solution of sodium hydroxide to the reaction liquid, (b) a method of removing only formic acid which would be distilled out from the reaction liquid at a low temperature by distillation under reduced pressure, by utilizing the difference of the boiling points of imidazole and formic acid, and (c) a method of comprising adding water to the reaction liquid, and removing formic acid as an azeotrope with water.

However, by method (a), the reaction liquid and the aqueous solution of sodium hydroxide did not separate from each other, but became a homogeneous layer. Another problem found of method (a) was that when a solvent such as chloroform or methyl isobutyl ketone was added to the reaction system in order to promote the separation, as much as more than 40% of the imidazole moves to the aqueous layer. Methods (b) and (c) have turned out to have the disadvantage that a large amount of the imidazole was distilled out into the distillate containing formic acid. It was inferred that this was attributed to the formation of a salt between formic acid and the imidazole in a 1:1 equivalent relation.

The removal of formic acid according to the present invention has been brought to light as a result of various examinations as mentioned above, and according to the present invention, formic acid is very advantageously removed from the reaction mixture.

Specifically, the removal of formic acid according to the present invention basically depends on heating the reaction mixture (reaction liquid) at 100°–250° C., to decompose and remove formic acid or esterifying formic acid in the reaction liquid with an alcohol and removing formic acid as a formic acid ester.

The heat treatment of the reaction liquid for decomposing and removing formic acid is carried out at a temperature of normally 100°–250° C., preferably 120°–200° C., more preferably 150°–200° C. The heat treatment period varies according to the amount of formic acid existing in the reaction liquid and the heating temperature, but normally it is about 3–15 hours. The heat treatment of the reaction liquid may be carried out under atmospheric pressure, under reduced pressure and under elevated pressure, but normally it is preferable to carry out the heat treatment under atmospheric or reduced pressure.

By heat treating the reaction liquid in such a way, it is possible to remove at least a greater part of formic acid in the reaction liquid.

It is desirable to reduce the amount of formic acid in the reaction liquid to less than 5% by weight, preferably less than 2% by weight.

When the reaction liquid containing formic acid is heat treated in such a manner as mentioned above, formic acid is thermally decomposed to produce carbon monoxide, carbon dioxide, hydrogen and water as shown in the following reaction formulae (C) and (D), of which carbon monoxide, carbon dioxide and hydrogen are removed as gaseous substances to the outside of the reaction system.

$$HCOOH \rightarrow CO + H_2O \quad (C)$$

$$HCOOH \rightarrow CO_2 + H_2 \quad (D)$$

At this time, water distills together with the gaseous substances and this distillate water is accompanied by part of formic acid.

It is also possible to accelerate removal by distillation of water, ammonia and formic acid from the reaction liquid by heating the reaction liquid containing formic acid under reduced pressure or blowing an inert gas (for example, $N_2$ or aqueous vapor) into the reaction liquid.

Formic acid is decomposed and removed, according to the present invention, by, as mentioned above, heating the reaction liquid at a temperature of 100°–250° C., by which formic acid is very effectively removed, whereas the desired compound, the imidazole, is hardly decomposed. For example, when the reaction liquid containing 16.5% by weight (1.41 mols) of formic acid and 23% by weight (1.1 mols) of 4-methylimidazole was heated at 190° C. for 10 hours, formic acid was decreased to 0.7% by weight (0.04 mol), but the desired product, 4-methylimidazole, remained in an amount of 1.03 mols in the reaction system, and the loss of the imidazole by heating of the reaction liquid was only 6.3%.

When the heating temperature for the decomposition of formic acid is less than 100° C., the decomposition rate of formic acid is undesirably too slow. On the other hand, when the heating temperature exceeds 250° C., the decomposition rate of formic acid is fast, but the desired product, the imidazole, is also undesirably decompose.

As mentioned above, by heating the reaction liquid, at least a greater part of formic acid in the reaction liquid can be decomposed and removed, but a small amount of formic acid may remain in the reaction liquid. However, by adding an alkali in an amount not less than an equivalent to this remaining formic acid, it is possible to advantageously remove this remaining formic acid. As the alkaline compound used in this case, there may be illustrated an alkali metal hydroxide such as sodium hydroxide and potassium hydroxide, an alkaline earth metal hydroxide such as calcium hydroxide and barium hydroxide or an aqueous solution of each of these metal hydroxides. Further, as required, by blowing ammonia gas into the reaction liquid, it is possible to remove the remaining formic acid in the reaction liquid. As mentioned above, it is preferable to make the amount of the alkaline compound to be added to formic acid not less than an equivalent of formic acid, and it is more preferable to use 1–3 equivalents of the compound per equivalent of formic acid. When too large an amount of the alkaline compound is used, a large amount of a metal salt will undesirably be contained in a distillation bottom obtained at the time of distillation of the reaction liquid to be mentioned later.

The method of esterifying formic acid in the reaction liquid with an alcohol and removing it as a formic acid ester is carried out as follows.

The alcohol to be reacted with formic acid is supplied to the reaction liquid by adding it to the reaction liquid. It is preferable to add 1–20 mols of the alcohol per mol of formic acid contained in the reaction liquid. Preferably, the alcohol is gradually or at once added to the reaction liquid after completion of the reaction. As required, however, it is possible to add the alcohol to the reaction liquid in advance.

The esterification reaction of formic acid and the alcohol is carried out normally at a temperature of 100°–200° C., preferably 120°–180° C. The heat treating period varies according to the amount of formic acid existing in the reaction liquid and the heating temperature, but normally it is about 1–10 hours. The esterification reaction of formic acid contained in the reaction liquid and the alcohol may be carried out under atmospheric pressure, under reduced pressure or under elevated pressure, but normally it is preferable to carry out the reaction under atmospheric or reduced pressure.

By subjecting formic acid in the reaction liquid to the esterification treatment with alcohols in such a manner, it is possible to decompose and remove at least a greater part of formic acid. Desirably, the amount of formic acid in the reaction liquid is decreased to less than 5% by weight, preferably less than 2% by weight.

The reaction of formic acid with the alcohol normally requires an esterification catalyst, but since in the present invention, the reaction product, the imidazole such as 4-methylimidazole functions as an esterification catalyst, it is not particularly necessary to add an esterification catalyst to the reaction liquid, while it is possible to add a basic esterification catalyst such as, for example, sodium hydroxide or potassium hydroxide to the reaction liquid.

As the alcohol used in the esterification reaction with formic acid, there may be specifically illustrated methanol, ethanol, n-propanol, isopropanol, n-butanol, sec-butanol, ethylene a glycol, diethylene glycol, triethylene glycol and propylene glycol.

When removal of formic acid contained in the reaction liquid is made by the esterification reaction with the alcohol, formic acid is very effectively removed, while the desired compound, the imidazole, is hardly decomposed thermally at the time of such esterification reaction.

Further, at the time of the esterification reaction of formic acid with the alcohol, formic acid is removed by the esterification reaction, and in addition, because the reaction liquid is heated at 100-200° C., part of formic acid undergoes thermal decomposition shown in reaction formulae (C) and (D).

By carrying out the esterification reaction as mentioned above, at least a greater part of formic acid in the reaction liquid can be decomposed and removed, but a small amount of formic acid may remain in the reaction liquid. This remaining formic acid may be removed by reaction (neutralization) with an alkaline compound. This neutralization reaction is carried out under the same conditions as mentioned above.

The reaction liquid so removed of formic acid is then distilled and the desired product, the imidazole, is separated. Because the distillation bottom obtained by distillation is very viscous, it may be difficult to handle. Accordingly, it is desirable to add a solvent to this bottom so as to make it less viscous. This solvent may be added to the bottom, or it may be added to the reaction liquid and the reaction liquid may be distilled under such conditions as to permit this solvent to remain in the bottom. As such a solvent, alcohols, glycols, glycerins and ketones are used.

As mentioned above, since according to the present invention, formic acid in the reaction liquid is almost completely removed, the separation equipment such as a distillation column is not corroded.

EFFECT OF THE PRESENT INVENTION

According to the reaction for producing imidazoles in accordance with present invention, an $\alpha$-hydroxycarbonyl compound (HC) and formamide (FA) are reacted under specified conditions. Accordingly, even if the FA/HC molar ratio is not more than 2, 2-unsubstituted imidazoles may be obtained in a very high yield. In addition, because FA is not used in a great excess in the reaction, the effect that a recovery operation accompanying decomposition of FA becomes unnecessary is obtained as well.

Figure 1:
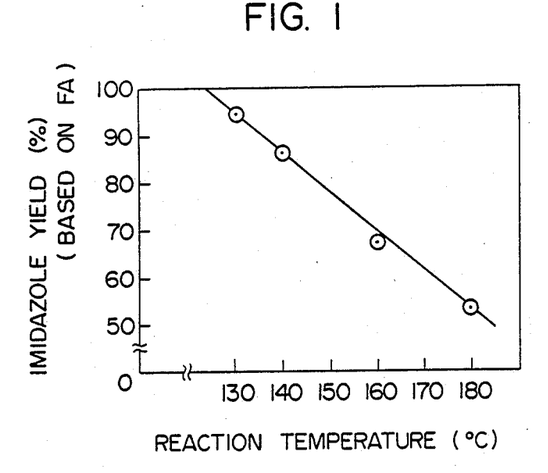
FIG. 1 is a diagram showing the relation between the reaction temperature and the imidazole yield.
Figure 2:
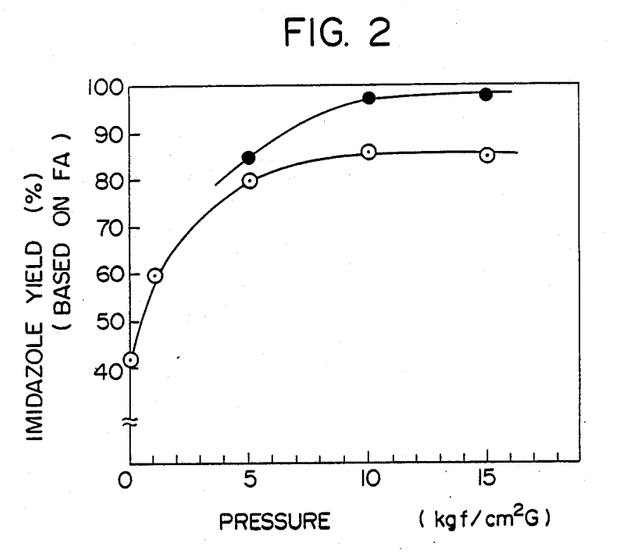
FIG. 2 is a diagram showing the relation between the ammonia pressure and the imidazole yield.
Figure 3:
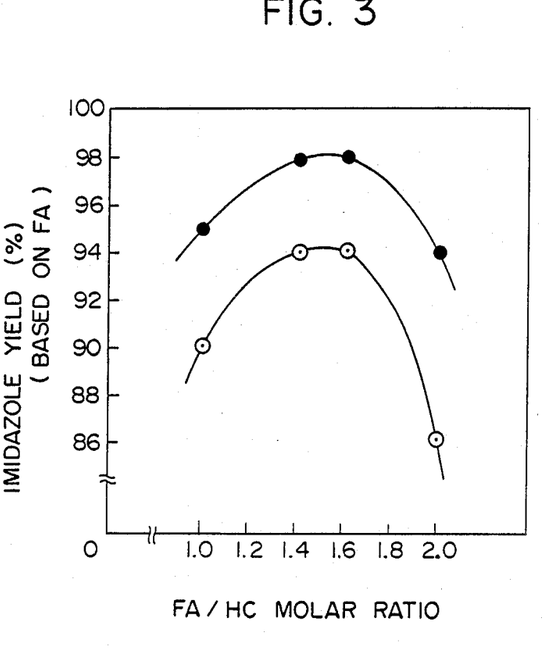
FIG. 3 is a diagram showing the relation between the FA/HC molar ratio and the imidazole yield.

The effects of the reaction of the present invention will be apparent from FIG. 1, FIG. 2 and FIG. 3.

In FIG. 1, the results of reacting FA with HC at an FA/HC molar ratio of 2 while ammonia gas is introduced under a pressure of 10 kgf/cm$^2$G to the reaction system at 130° C. for 20 hours, at 140° C. for 10 hours, at 160° C. for 6 hours and at 180° C. for 4 hours are shown as the relation of the reaction temperature and the imidazole yield (based on FA).

In FIG. 2, the results of reacting FA with HC at an FA/HC molar ratio of 2 at 130° C. for 20 hours and at 140° C. for 10 hours at the ammonia gas pressure of 0, 1, 5, 10 and 15 kgf/cm$^2$G are shown as the relation of the ammonia gas pressure and the imidazole yield (based on FA). In FIG. 2, ● shows the case of reactions at 130° C., for 20 hours and ● shows the case of reactions at 140° C. for 10 hours.

Further, in FIG. 3, the results of reacting FA with HC at an ammonia gas pressure of 10 kgf/cm$^2$G at 130° C. for 20 hours and at 140° C. for 10 hours at FA/HC molar ratio of 1.0, 1.4, 1.6 and 2.0 are shown as the relation of the FA/HC molar ratio and the imidazole yield (based on FA).

In FIG. 3, ● shows the case of reactions at 130° C. for 20 hours and o shows the case of reactions at 140° C. for 10 hours.

By a process for preparing imidazoles according to the present invention, because formic acid produced as a by-product in the reaction is removed, the reactor or the separation equipment such as a distillation column is not corroded. Moverover, imidazoles of a high purity can be obtained.

BEST MODE FOR PRACTICING THE INVENTION

Hereinbelow, the present invention will be explained by way of examples. It should be noted however that the present invention is not limited to these examples.

EXAMPLE 1

A 300-milliliter flask equipped with a stirrer, a thermometer, a dropping funnel, an NH$_3$ gas blowing pipe and a reflux condenser was charged with 2 mols of formamide, and while blowing $NH_3$ gas into the flask at 160° C. under atmospheric pressure, 1 mol of hydroxyacetone was added dropwise to formamide from the dropping funnel. The total amount of $NH_3$ gas blown was 1.6 mols.

In the so obtained reaction liquid, 0.51 mol (51% of the theoretical amount) of 4-methylimidazole was produced.

EXAMPLE 2

A 300-milliliter autoclave equipped with a stirrer, a thermometer, a pressure gauge, a hydroxyacetone feed line and an $NH_3$ gas feed line was charged with 2 mols of formamide, and after the temperature was elevated to 160° C., the pressure inside the reactor was elevated to 10 kgf/cm$^2$G with $NH_3$ gas. Subsequently, 1 mol of hydroxyacetone was added to formamide by a pump over 6 hours. The pressure gradually lowered and became 4 kg/cm$^2$G after 2 hours, then began to rise and became 18 kg/cm$^2$G after 6 hours.

In the so obtained reaction liquid, 0.62 mol (62% of the theoretical amount) of 4-methylimidazole was produced.

EXAMPLE 3

A 300-milliliter autoclave equipped with a stirrer, a thermometer, a hydroxyacetone feed line, an $NH_3$ gas feed line, a pressure gauge and a pressure regulating valve was charged with 2 mols of formamide, and while blowing $NH_3$ gas into the reactor at 160° C. under the pressure of 15 kg/cm$^2$G, 1 mol of hydroxyacetone was added to formamide by a pump over 6 hours. Water produced as a by-product and part of $NH_3$ gas were withdrawn through the pressure regulating valve to the outside of the system. The total amount of $NH_3$ gas blown was 3.0 mols.

In the so obtained reaction liquid, 0.69 mol (69% of the theoretical amount) of 4-methylimidazole was produced.

EXAMPLE 4

The autoclave used in Example 2 was charged with 2 mols of formamide and after the temperature was elevated to 140° C., the pressure inside the reactor was elevated to 10 kg/cm$^2$G with $NH_3$ gas. Subsequently, 1 mol of hydroxyacetone was added to formamide by a pump over 10 hours, while at the same time, continuously supplying $NH_3$ gas pressurized to 10 kg/cm$^2$G to the reactor during the reaction. The pressure inside the reactor was constant at 10 kg/cm$^2$G. The total amount of $NH_3$ gas supplied was 1.3 mols.

In the so obtained reaction liquid, 0.86 mol (86% of the theoretical amount) of 4-methylimidazole was produced.

EXAMPLE 5

The autoclave used in Example 2 was charged with 1.6 mols of formamide and after the temperature was elevated to 130° C., the pressure inside the reactor was elevated to 10 kg/cm$^2$G with $NH_3$ gas. Subsequently, 1 mol of hydroxyacetone was added to formamide by a pump over 20 hours, while at the same time, continuously supplying $NH_3$ gas pressurized to 10 kg/cm$^2$G into the reactor during the reaction. The pressure inside the reactor was constant at 10 kg/cm$^2$G. The total amount of $NH_3$ gas supplied was 1.5 mols.

In the so obtained reaction liquid, 0.78 mol (98% of the theoretical amount to formamide, 78% of the theoretical amount to hydroxyacetone) of 4-methylimidazole was produced.

COMPARATIVE EXAMPLE 1

The flask used in Example 1 was charged with 2 mols of formamide, to which 1 mol of hydroxyacetone was added dropwise through the dropping funnel at 180° C. under atmospheric pressure over 4 hours.

In the so obtained reaction liquid, only 0.33 mol (33% of the theoretical amount) of 4-methylimidazole was produced.

COMPARATIVE EXAMPLE 2

The autoclave used in Example 2 was charged with 2 mols of formamide and after the temperature was elevated to 180° C. in an $N_2$ atmosphere, the reaction system was sealed under atmospheric pressure. Subsequently, 1 mol of hydroxyacetone was added by a pump to formamide over 4 hours. The pressure gradually rose from the atmospheric pressure and became 23 kg/cm$^2$G after 4 hours.

In the so obtained reaction liquid, only 0.39 mol (39% of the theoretical amount) of 4-methylimidazole was produced.

EXAMPLE 6 [Reaction step]

A 3-m$^3$ glass-lined pressure reactor was charged with 800 kg (17.8 kmols) of formamide and after the temperature was elevated to 130° C. with stirring in an $NH_3$ gas atmosphere, the pressure inside the system was elevated with 10 kg/cm$^2$G $NH_3$ gas and the system was sealed. Next, total 1550 kg (11.1 kmols) of hydroxyacetone (composition: 53% hydroxyacetone, 32% water, 8% phenol, 5% others) recovered by separation from the cumene method phenol process was added at a rate of 77.5 kg/hr to formamide with stirring over 20 hours. During addition of hydroxyacetone, pressurized $NH_3$ gas was always supplied to the reaction system to keep the pressure inside the system at 10 kg/cm$^2$G. The total amount of $NH_3$ gas supplied was 240 kg. In 2590 kg of the reaction liquid obtained after cooling the system to room temperature, 25.0% (648 kg) of 4-methylimidazole and 14.3% (370 kg) of formic acid were produced. [Step of removing formic acid by decomposition]

Next, the reaction liquid was gradually heated under atmospheric pressure with stirring in said reactor, and after the pressure was reduced halfway to 500 mmHg, when the reaction liquid was kept at 100° C., total 1050 kg of a distillate flowed out. The distillate consisted predominantly of water and $NH_3$, and contained 4.6% (48 kg) of formic acid. At this point, the concentration of formic acid in 1540 kg of the reaction liquid remained in the reactor was 20.9%. Next, the heating was further continued under atmospheric pressure, and after the reaction temperature reached 180° C., the stirring was continued at the same temperature for 8 hours. During the period, when the reaction temperature was in the vicinity of 150° C., formic acid began to be decomposed, continuously emitting a gas consisting mainly of CO, $CO_2$ and $H_2$. The amount of the reaction liquid after 8 hours was 980 kg that contained 1.4% (13.7 kg) of formic acid and 63.4% (621 kg) of 4-methylimidazole. Namely, the removing ratio of formic acid in this step was $$\frac{370 - 13.7}{370} \times 100 = 96.3\%,$$

and the recovery ratio of 4-methylimidazol was $$\frac{621}{648} \times 100 = 95.8\%.$$

[Step of removing formic acid by neutralization]

Next, the reaction liquid was cooled to 50° C. in the reactor, to which 71.4 kg of a 25% aqueous solution of NaOH [NaOH/formic acid (equivalent ratio)=1.5] was added, and the mixture was stirred for 30 minutes. [Step of distillation and purification]

Next, to the reaction liquid in the reactor was added 200 kg of triethylene glycol, and well mixed. The mixture was distilled batch-wise by SUS316L distillation equipment having 20 theoretical plates under conditions of a column top pressure of 20 mmHg and a reflux ratio of 0–10. When a fraction of the distillate at a column top temperature of 158°–160° C. was recovered, 565 kg of 4-methylimidazole having a purity of more than 98% was obtained. The bottom was a liquid having sufficient fluidity at room temperature and could be easily handled. After completion of the distillation, the presence of corrosion at each portion of the distillation equipment was examined, but no corrosion whatsoever was recognized.

The recovery ratio of 4-methylimidazole in the distillation step was $$\frac{565}{621} \times 100 = 91.0\%.$$

EXAMPLE 7

A 300-milliliter distillation flask equipped with a stirrer, a thermometer, a feed pipe, a Liebig condenser, an adapter and a receiver was charged with 80 g of a reaction liquid, obtained by the reaction of hydroxyacetone with formamide, consisting of 28% by weight of 4-methylimidazole, 17% by weight of formic acid, 11% by weight of ammonia, 3% by weight of formamide, 36% by weight of water and 5% by weight of others, and the liquid was heated at 150° C. with stirring.

While keeping the reaction liquid at 150° C., 80 g of methanol was supplied to the reaction liquid using a metering pump through the feed pipe in 4 hours to esterify formic acid. A vapor generated at this time was condensed by the Liebig condenser with flowing ice water and collected in the receiver.

The concentration of formic acid in the so obtained reaction liquid was measured. And the resulting ester was determined by analyzing of the condensed liquid in the receiver by gas chromatograpy and mass spectrometry.

The results are shown in Table 1.

Next, to the reaction liquid in which formic acid was so esterified were added triethylene glycol and 2 equivalents, per equivalent of formic acid contained in the reaction liquid, of sodium hydroxide. They were well mixed and the mixed liquid was distilled batchwise by a distillation device made of corrosion resistant steel (SUS316L) and having 20 theoretical plates under conditions of a column top pressure of 20 mmHg and a reflux ratio of 0–10. When a fraction of the distillate at a column top temperature of 158°–160° C. was recovered, 4-methylimidazole having a purity of more than 98% was obtained. The recovery ratio of 4-methylimidazole at this time is shown in Table 1.

The bottom was a liquid having a sufficient fluidity at room temperature and could be easily handled. After completion of the distillation, the presence of corrosion at each portion of the distillation equipment was examined, but no corrosion whatsoever was recognized.

Example 8

Example 7 was repeated except that the esterification reaction of formic acid and methanol was carried out while the reaction liquid was kept at 120° C.

The results are shown in Table 1.

EXAMPLE 9

Example 7 was repeated except that the amount of methanol supplied was changed to 40 g. The results are shown in Table 1.

EXAMPLE 10

Example 7 was repeated except that ethanol was used instead of methanol. The results are shown in Table 1.

EXAMPLE 11

Example 7 was repeated except that isopropanol was used instead of methanol. The results are shown in Table 1.

EXAMPLE 12

Example 7 was repeated except that n-propanol was used instead of methanol. The results are shown in Table 1.

TABLE 1

| Example | Concentration of formic acid | Recovery ratio of 4-methylimidazole | Produced ester |
|---|---|---|---|
| 7 | 0.4% | 91% | Methyl formate |
| 8 | 2.7% | 99% | Methyl formate |
| 9 | 1.5% | 94% | Methyl formate |
| 10 | 0.9% | 91% | Ethyl formate |
| 11 | 2.6% | 97% | Isopropyl formate |
| 12 | 1.8% | 92% | n-Propyl formate |

We claim:

1. A process for preparing 2-unsubstituted imidazoles represented by the following general formula (II)

$$\begin{array}{c} R^1-C-\!\!\!-\!\!\!-N \\ \parallel \quad\quad \parallel \\ R^2-C \quad\quad CH \\ \diagdown \diagup \\ N \\ | \\ H \end{array} \quad (II)$$

wherein $R^1$ and $R^2$ may be the same or different, and each represents: a hydrogen atom, an alkyl 1 to 14 carbon atoms; a cycloalkyl group having a carbon ring member of 4 to 8 carbon atoms, which may be unsubstituted or substituted by an alkyl group of 1 to 3 carbon atoms; an aryl group selected from the group consisting of phenyl, naphthyl and anthranyl, wherein said phenyl naphthyl or anthranyl may be unsubstituted or substituted by an alkyl group of 1 to 10 carbon atoms or an alkoxy group of 1 to 10 carbon atoms; or an arylalkyl group wherein said aryl moiety is selected from the group consisting of phenyl, naphthyl and anthranyl, wherein said phenyl, naphthyl or anthranyl may be unsubstituted or substituted by an alkyl group having 1 to 10 carbon atoms or an alkoxy group of 1 to 10 carbon atoms, and said alkyl moiety of said arylalkyl group has 1 to 14 carbon atoms; said process comprising:

reacting an α-hydroxycarbonyl compound represented by the following formula (I)

(I)

ps wherein $R^1$ and $R^2$ are the same as defined above, with a formamide at a reaction temperature of 100°–170° C. in an atmosphere of ammonia gas, wherein the molar ratio of said formamide to said α-hydroxycarbonyl compound is not more than 2.

2. A process according to claim 1, wherein said reaction temperature is 130°–140° C.

3. A process according to claim 1, wherein the partial pressure of said ammonia gas in the reaction atmosphere is 5–15 kgf/cm$^2$G.

4. A process according to claim 1, wherein the reaction is carried out while said β-hydroxycarbonyl compound in an amount to provide said specified ratio is being gradually added to the formamide charged in a reactor.

5. A process according to claim 1, wherein after said reaction of the β-hydroxycarbonyl compound with the formamide, formic acid formed as a by-product by said reaction is removed from the reaction mixture.

6. A process according to claim 5, wherein said reaction mixture is heated at a temperature of 100°–250° C. to thermally decompose and remove formic acid.

7. A process according to claim 5, wherein said reaction mixture is heated at a temperature of 120°–200° C. to thermally decompose and remove formic acid.

8. A process according to claim 5, wherein said reaction mixture is heated at a temperature of 100°–250° C. to thermally decompose and remove a greater part of formic acid, and then the remaining formic acid is neutralized with an alkaline compound and removed.

9. A process according to claim 8, wherein said reaction mixture is heated at a temperature of 120°–200° C. to thermally decompose and remove a greater part of said formic acid.

10. A process according to claim 8, wherein said alkaline compound is an alkali metal hydroxide or an alkaline earth metal hydroxide.

11. A process according to claim 5, wherein formic acid in said reaction mixture is esterified with an alcohol and removed as a formic acid ester.

12. A process according to claim 11, wherein said esterification is carried out at a temperature of 100°–200° C.

13. A process according to claim 5, wherein a greater part of formic acid is esterified with an alcohol and removed as a formic acid ester, and then the remaining formic acid is neutralized with an alkaline compound and removed.

14. A process according to claim 13, wherein said esterification is carried out at a temperature of 100°–200° C.

* * * * *

UNITED STATES PATENT AND TRADEMARK OFFICE
CERTIFICATE OF CORRECTION

PATENT NO. : 4,891,431
DATED : January 2, 1990
INVENTOR(S) : SANEHIRO YAMAMOTO ET AL.

It is certified that error appears in the above-identified patent and that said Letters Patent is hereby corrected as shown below:

Claim 1, line 8 of the claim, after "alkyl", insert --group having--;
line 28 of the claim, "ps" should be deleted.
Claim 4, line 2 of the claim, "β-hydroxycarbonyl" should read --α-hydroxycarbonyl--.
Claim 5, line 2 of the claim, "β-hydroxycarbonyl" should read --α-hydroxycarbonyl--.

Signed and Sealed this

Nineteenth Day of February, 1991

*Attest:*

HARRY F. MANBECK, JR.

*Attesting Officer*     *Commissioner of Patents and Trademarks*